United States Patent
Kallivretaki et al.

(10) Patent No.: US 11,235,485 B2
(45) Date of Patent: Feb. 1, 2022

(54) SHAVING AID FOR RETAINING ELEMENTS

(71) Applicant: BIC VIOLEX S.A., Anixi Attikis (GR)

(72) Inventors: Argyro Kallivretaki, Anixi Attikis (GR); Panagiotis Moustakas, Athens (GR); Georgios Tsiakatouras, Anixi Attikis (GR)

(73) Assignee: BIC VIOLEX S.A., Anixi Attikis (GR)

( * ) Notice: Subject to any disclaimer, the term of this patent is extended or adjusted under 35 U.S.C. 154(b) by 71 days.

(21) Appl. No.: 16/392,042

(22) Filed: Apr. 23, 2019

(65) Prior Publication Data

US 2020/0338769 A1 Oct. 29, 2020

(51) Int. Cl.
*B26B 21/44* (2006.01)
*B26B 21/40* (2006.01)
*A61Q 19/00* (2006.01)
*A61K 8/86* (2006.01)

(52) U.S. Cl.
CPC ............. *B26B 21/44* (2013.01); *A61K 8/86* (2013.01); *A61Q 19/00* (2013.01); *B26B 21/4012* (2013.01); *B26B 21/4018* (2013.01)

(58) Field of Classification Search
CPC .................................. A61K 8/86; A61Q 19/00
See application file for complete search history.

(56) References Cited

U.S. PATENT DOCUMENTS

| | | | | |
|---|---|---|---|---|
| 4,996,772 A | * | 3/1991 | Iten | B26B 21/4037 30/123.3 |
| 5,369,885 A | * | 12/1994 | Ferraro | B26B 21/4018 30/41 |
| 5,579,580 A | * | 12/1996 | Althaus | B26B 21/22 30/50 |
| 5,626,154 A | * | 5/1997 | Rogers | B26B 21/443 132/200 |
| 5,713,131 A | | 2/1998 | Rogers et al. | |
| 6,216,345 B1 | | 4/2001 | Andrews | |
| 6,298,558 B1 | * | 10/2001 | Tseng | B26B 21/443 30/41 |
| 6,996,908 B2 | * | 2/2006 | Orloff | A45D 27/04 30/41 |
| 7,581,318 B2 | * | 9/2009 | Coffin | B26B 21/443 30/41 |
| 8,236,214 B2 | | 8/2012 | Kwiecien | |

(Continued)

FOREIGN PATENT DOCUMENTS

CN 105219007 1/2016
EP 0551407 7/1993

(Continued)

*Primary Examiner* — Andrea L Wellington
*Assistant Examiner* — Fernando A Ayala
(74) *Attorney, Agent, or Firm* — Ohlandt, Greeley, Ruggiero and Perle, LLP

(57) ABSTRACT

A razor cartridge includes a housing having a portion that forms a cavity and a retaining element configured to maintain a blade in the housing. The retaining element has a top portion that includes an aperture therethrough, a bottom portion, and an intermediate portion connecting the top portion to the bottom portion to define an interior volume between the top portion and the bottom portion. The cavity is fitted with a shaving aid. The retaining element is connectable to the housing so that the shaving aid is encompassed by the interior volume of the retaining element.

20 Claims, 11 Drawing Sheets

(56) References Cited

U.S. PATENT DOCUMENTS

| | | | |
|---|---|---|---|
| 9,044,429 B2* | 6/2015 | Bakes | A61Q 9/02 |
| 9,539,734 B1 | 1/2017 | Bozikis et al. | |
| 9,738,000 B2 | 8/2017 | Ariyanayagam et al. | |
| 10,532,476 B1 | 1/2020 | Skarmoutsou et al. | |
| 2006/0254056 A1* | 11/2006 | Coffin | B26B 21/44 |
| | | | 30/41 |
| 2009/0223057 A1 | 9/2009 | Coope-Epstein et al. | |
| 2012/0000074 A1* | 1/2012 | PazosSchroeder | B26B 21/4087 |
| | | | 30/34.05 |
| 2012/0023749 A1 | 2/2012 | Ariyanayagam et al. | |
| 2012/0023750 A1 | 2/2012 | Blatter et al. | |
| 2013/0008029 A1 | 1/2013 | Hill et al. | |
| 2013/0042482 A1 | 2/2013 | Bradford et al. | |
| 2013/0153135 A1* | 6/2013 | Burgio | B29C 39/025 |
| | | | 156/242 |
| 2016/0338928 A1 | 11/2016 | Haught et al. | |
| 2017/0151683 A1* | 6/2017 | Bozikis | B26B 21/4025 |
| 2018/0361604 A1 | 12/2018 | Bozikis et al. | |

FOREIGN PATENT DOCUMENTS

| | | |
|---|---|---|
| EP | 2488330 | 8/2012 |
| EP | 2488331 | 8/2012 |
| EP | 2488332 | 8/2012 |
| EP | 2490868 | 8/2012 |
| EP | 2576673 | 4/2013 |
| WO | 9205925 | 4/1992 |
| WO | 2011/047221 | 4/2011 |

* cited by examiner

SHAVING AID FOR RETAINING ELEMENTS

BACKGROUND

1. Field

The present disclosure relates to retaining elements for a razor cartridge having a shaving aid dispenser assembly. The disclosure further relates to razor cartridges including such retaining elements and to razors or razor assemblies including such cartridges with a shaving aid dispenser assembly.

2. Description of Related Art

Razors generally predate the common era. Disposable razors have been generally known since the second half of the 20th Century. Disposable safety razors are constructed from materials that are inexpensive and are meant to be disposable when the blades dull, commonly after one or more uses. Since blade sharpening or replacement is not a feasible option for extending the life of a disposable razor, incorporating blades with long-lasting properties or providing other razor components with enhanced durability may be useful in prolonging the life of a disposable razor thereby allowing for an increase in the number of times that the razor may be re-used.

SUMMARY

The present disclosure provides a razor cartridge that includes a housing having a portion that forms a cavity and a retaining element configured to maintain a blade in the housing. The retaining element has a top surface that includes an aperture therethrough, a bottom surface, and a side portion connecting the top surface to the bottom surface to define a volume between the top surface and the bottom surface. The retaining element is connectable to the housing so that the cavity of the housing is fitted in the volume of the retaining element and a shaving aid is fitted in the cavity of the housing.

The present disclosure also provides a razor cartridge that includes a housing having a portion forming a cavity. A retaining element is configured to maintain one or more blades in the housing. The retaining element has a top portion that includes an aperture therethrough, a bottom portion, and an intermediate portion connecting the top portion to the bottom portion to define a volume between the top portion and the bottom portion. The retaining element is connectable to the housing of the cartridge. A shaving aid is provided in the cavity of housing. The shaving aid includes a lubricating composition and a pusher material.

The present disclosure further provides a razor cartridge that includes a housing having a portion forming a cavity. A retaining element is configured to maintain one or more blades in the housing. The retaining element has a top portion that includes an aperture therethrough, a bottom portion, and an intermediate portion connecting the top portion to the bottom portion to define a volume between the top portion and the bottom portion. The retaining element is connectable to a side edge of the housing. A shaving aid is provided in the cavity of the housing and a retaining element is attached to the housing.

The above summary is not intended to describe each disclosed implementation. In particular, selected features in this disclosure may be incorporated into additional features as detailed herein below unless clearly stated to the contrary.

BRIEF DESCRIPTION OF THE DRAWINGS

The present disclosure will be more completely understood in consideration of the following detailed description in connection with the accompanying drawings, in which.

The accompanying drawings illustrate aspects of the present disclosure, and together with the general description given above and the detailed description given below,

DETAILED DESCRIPTION

Figure 1:
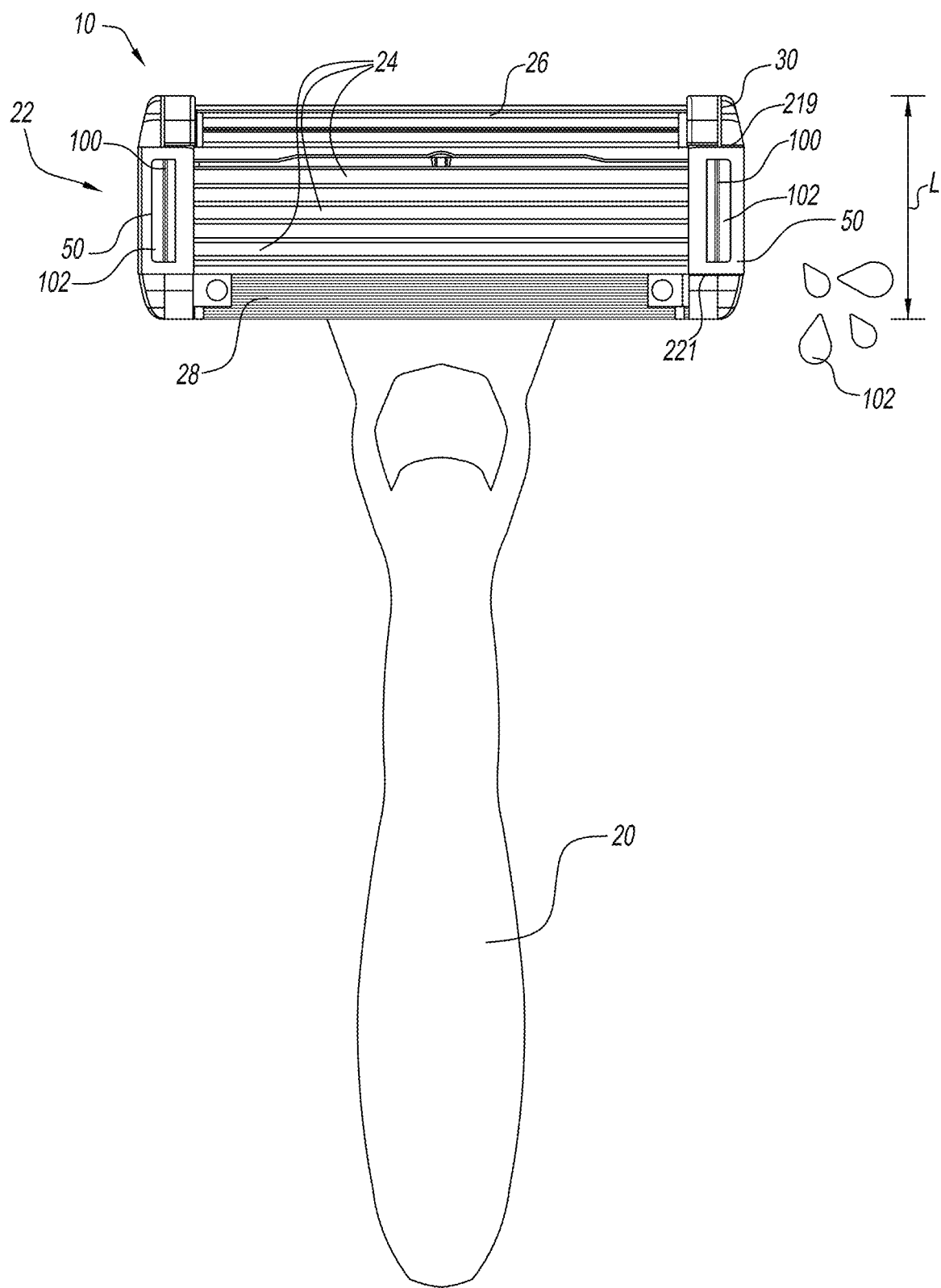
FIG. 1 is a front view of a razor having a cartridge with dispenser assemblies.
Figure 4A:
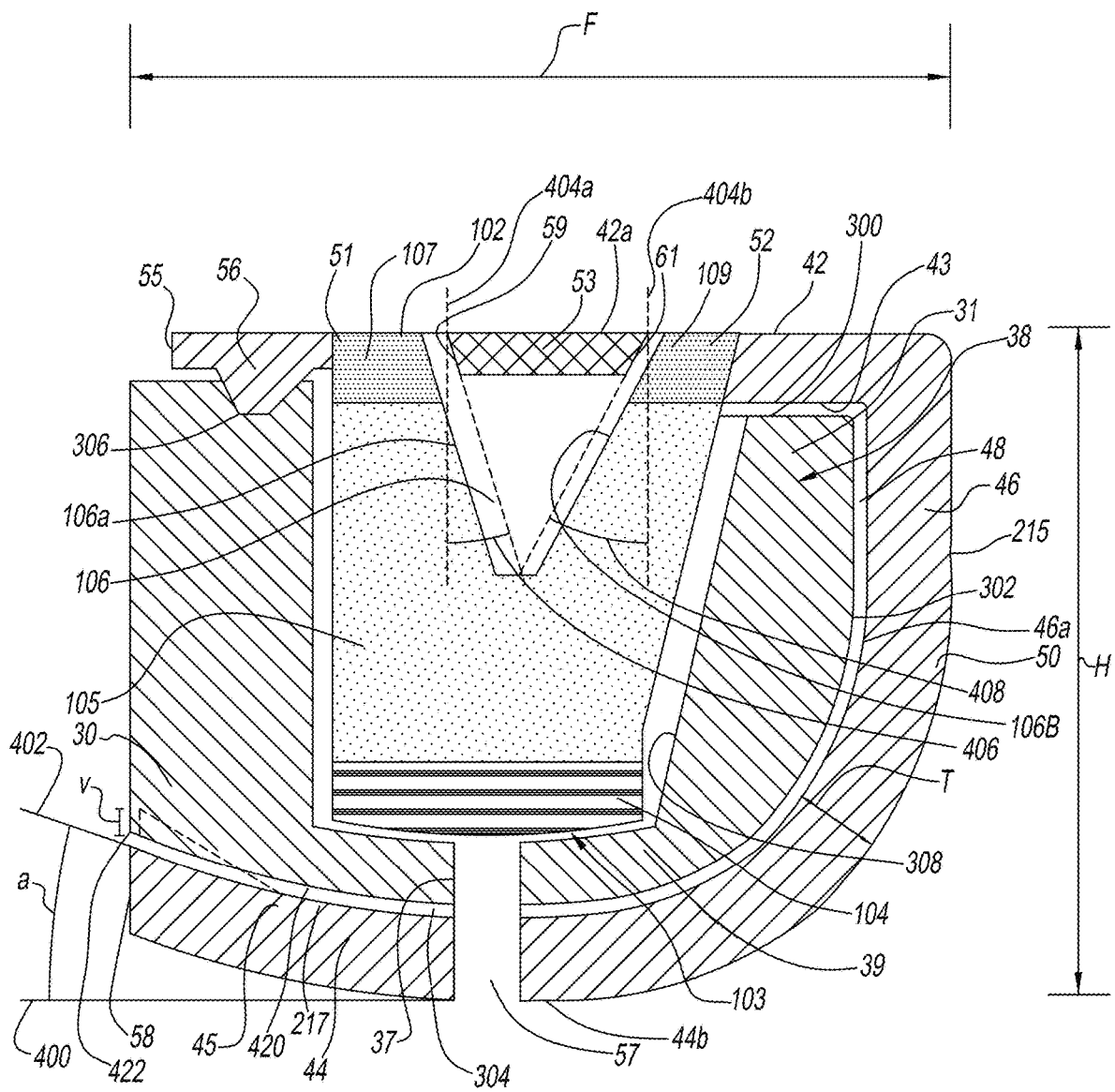
FIG. 4A is a side, cross-sectional view of a portion of the cartridge shown in FIG. 2 taken along line A-A.

Referring to the drawings and, in particular, to FIG. 1, there is shown a razor assembly or razor for shaving according to the present disclosure and generally represented by reference numeral 10. Razor 10 has an elongate handle 20 for grasping with a hand. Handle 20 is directly or indirectly connected to a cartridge 22. Cartridge 22 includes a housing 30, retaining element 50 for one or more razor blades 24 and a dispenser assembly 100 for dispensing a shaving aid, such as, a lubricating element or composition 102 including a pusher material 103 as shown in FIG. 4A.

Shaving aids include, but are not limited to, a lubricant, a moisturizer, a conditioner, an emollient or any combinations thereof.

Lubricating composition 102 is a skin lubricating composition that enhances glideness and/or lubricity of razor 10 during use. The lubricating composition 102 can act as a hair softener to facilitate cutting or the lubricating composition 102 can provide glideness, depending on the formulation. Lubricating composition 102 optionally delivers a cosmetic ingredient to the skin achieving skin benefits that include hydration, soothing, and the like. Pusher material 103 is a superabsorbent polymer or other material that can swell.

The dispenser assembly 100 provides a lubricating surface area 101. This lubricating surface area 101 can provide lubrication on at least one area or in some aspects in multiple areas, without increasing or substantially increasing, the conventional dimension of cartridge 22.

Figure 2:
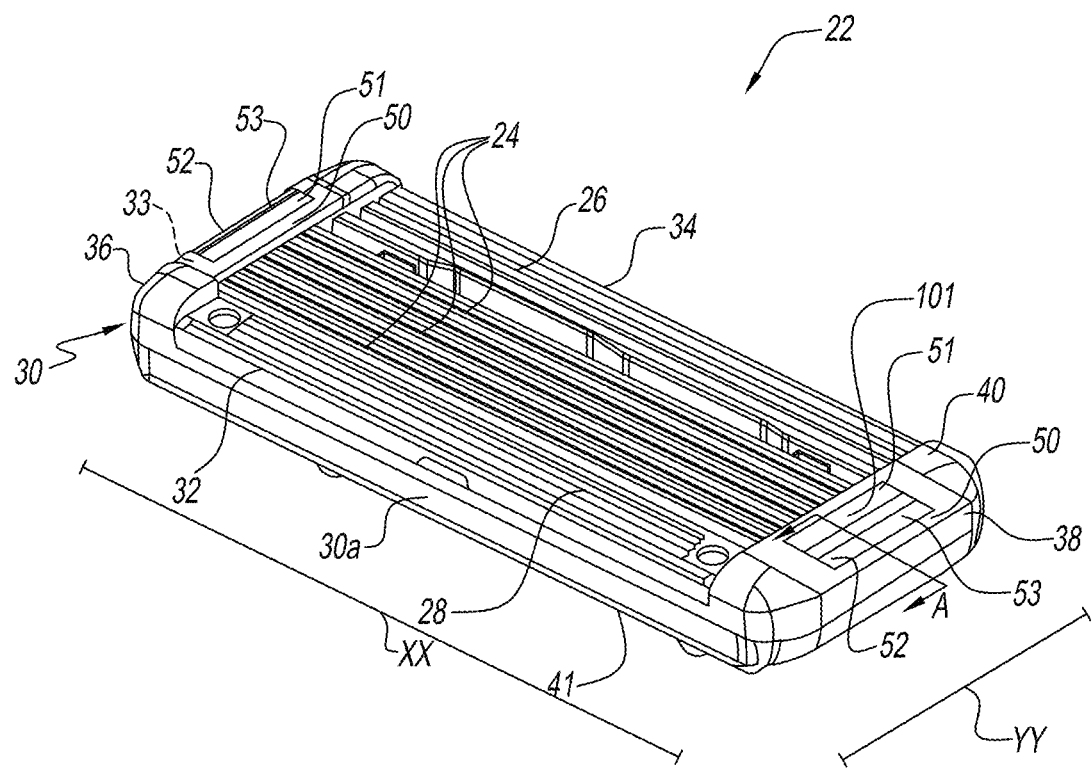
FIG. 2 is a perspective view of the cartridge with dispenser assemblies shown in FIG. 1.

Referring to FIG. 2, housing 30 has a front edge 32, a rear edge 34, a pair of side edges 36, 38, a top surface 40, and a bottom surface 41. The front edge 32 and rear edge 34 extends between the pair of sides 36, 38 from top surface 40 to bottom surface 41 to define a pair of longitudinal surfaces XX (only one being shown in FIG. 2). The pair of side edges 36, 38 extend between front edge 32 and rear edge 34 from top surface 40 to bottom surface 41 to define, respectively, a pair of lateral surfaces YY (only one being shown in FIG. 2). Thus, the pair of lateral surfaces YY extend from top surface 40 to bottom surface 41. In other words, the pair of side edges 36, 38 connects front edge 32 to rear edge 34 such that the longitudinal surfaces XX and the lateral surfaces YY are perpendicular. In some examples, top surface 40 can be a skin engaging surface. The one or more blades 24 can be secured in housing 30 between side edges 36 and 38 by one or more retaining elements 50.

Retaining elements 50 can be, for example, any suitably-configured component that can be attached on or cover the housing 30 either unitarily or partially. Specifically, retaining elements 50 can be, for example, any suitably configured component that can be attached to and cover the lateral surface YY of the housing 30 either unitarily or partially. According to some aspects, each retaining element 50 is a retaining element for each one of the one or more blade 24. Retaining elements 50 can also include, but are not limited to, skin adaptors, auxiliary devices that provide extended skin engaging surfaces and/or inner free volumes or compartments, lubricating frames, such as boxes with embedded cavities, such as containers or customizing tools having free spaces or volumes.

Figure 3:
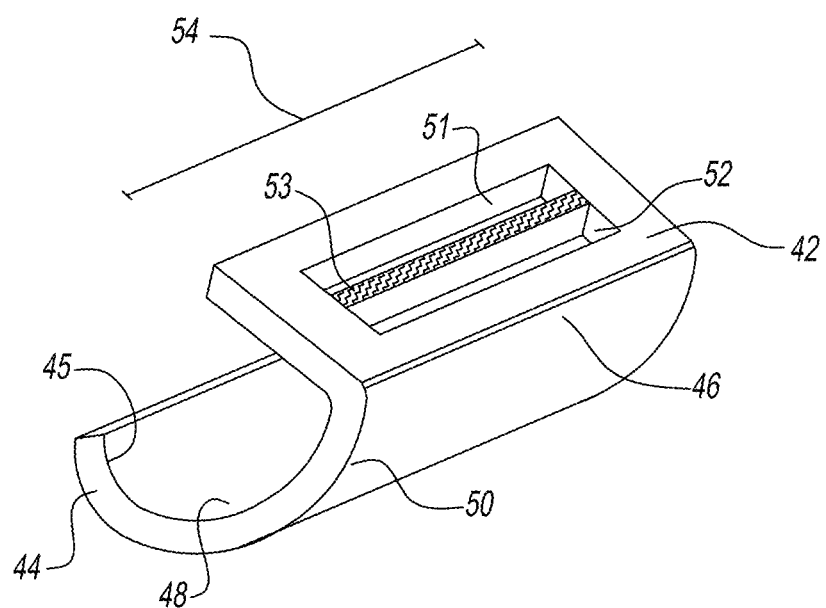
FIG. 3 is a side perspective view of a retaining element for the cartridge shown in FIG. 2.

Referring to FIG. 3, retaining element 50 includes a top portion 42 opposite a bottom portion 44. Top portion 42 and bottom portion 44 are joined together by an intermediate portion 46 and forms a C-shape. The C-shape defines an interior volume 48 of retaining element 50. Retaining element 50 has a width 54. Retaining element 50 embraces at least in part lateral surface YY and extends along a substantial portion of side edge 36, 38 of the housing 30. Retaining element 50 has a first aperture 51 and a second aperture 52 through top portion 42 separated by a bar 53.

As shown in FIGS. 4A-F, intermediate portion 46 is detailed as having an arcuate shape. An arcuate shape can be used, for example, to maximize interior volume 48. According to other aspects, intermediate portion 46 can have, for example, a parabolic shape, a hyperbolic shape, or a convex shape. In general, intermediate portion 46 can be any shape suitable for creating interior volume 48 for encompassing lubricating composition 102 and pusher material 103 that form the shaving aid. At least a portion of the top portion 42 is planar. However, according to other aspects, at least a portion of top portion 42 can be arcuate. Retaining element 50 has a projection 56 on a top interior surface 43 of top portion 42.

Side edge 38 of housing 30 has a receiving portion 31 that mates with retaining element 50. Receiving portion 31 is shaped to fit within and to mate with at least a portion of retaining element 50. Receiving portion 31 has a top side 300 that is complementary in shape to top interior surface 43, an outer side 302 that is complementary in shape to intermediate portion 46, and bottom side 304 that is complementary in shape to an interior bottom surface 45 of bottom portion 44. Receiving portion 31 has a groove 306 that is complementary in shape to and mates with projection 56 by snap fit. Bottom portion 44 of retaining element 50 follows the shape of housing 30 and deflects during the snap-fit assembly process. While projection 56 is only shown on top interior surface 43, there is no interlocking feature at interior bottom surface 45 of bottom portion 44 of retaining element 50. Retaining element 50 is made of a metal sheet that is folded in C-shape form and conforms to housing 30 during the assembly process, so as to engage housing 30 and is maintained therewith by groove 306 interacting with projection 56. In other examples, an additional bottom projection extending from interior bottom surface 45 is possible, as well as a projection extending from only bottom interior surface 45 or extending only from interior surface 46a of intermediate portion 46. Additionally, housing 30 includes an undersurface 420 and is molded with an indent 422 formed on the undersurface 420. Indent 422 on undersurface 420 is shaped to receive bottom portion 44 of retaining element 50. In some examples, indent 422 is shaped to receive projection (not shown) extending from interior bottom surface 45 of retaining element 50.

The one or more retaining elements 50 can be a pair of retaining elements 50. Each one of the pairs of retaining elements 50 is spaced apart and mounted, respectively, on the pair of side edges 36, 38 of housing 30 and on either side of the one or more blades 24. According to some aspects, retaining element 50 extends partially along a length L of the side edges 36, 38, for example, about 8.5 millimeters, and can include top portion 42 that extends above top surface 40 of housing 30 and over the one or more blades 24 to retain the one or more blades 24 in position within housing 30. According to some aspects, retaining elements 50 can be modified to extend along a shorter or a longer portion of side edges 36, 38, without deviating from the scope of the present disclosure. For example, one or both retaining elements 50 can be modified to extend along an entire length, a shorter portion, or a longer portion of side edges 36, 38. Any number of retaining elements 50, e.g., a single retainer or four retainers, can be used to secure the one or more blades 24 or other components of razor 10 in position within housing 30.

Retaining element 50 can include a first end 55, on top portion 42 and a second end 58, on bottom surface 44. Each of the first and second ends 55, 58 generally face toward the blades 24. The first end 55 is substantially planar, and the second end 58 is substantially rounded. The second end 58 can include a curvature defined by a plurality of radii inclusive of, for example, between 0.1 millimeters and 0.25 millimeters. According to some aspects, second end 58 has a curvature for example, between 0.15 millimeters and 0.2 millimeters. According to other aspects, either or both of the first and second ends 55, 58 are rounded, planar, or a combination thereof, without deviating from the scope of the present disclosure. An outer surface 215 of retaining element 50 can extend entirely between the first and second ends 55, 58 and along top portion 42, bottom portion 44 and intermediate portion 46. Opposite outer surface 215 of retaining element 50, is an inner surface 217. Inner surface 217 can extend entirely between the first and second ends 55, 58 and along the top portion 42, bottom portion 44 and intermediate portion 46 to directly abut, and substantially surround, side edge 38 of housing 30 of cartridge 100. Retaining element 50 can further include a rear edge 219 that is immediately adjacent or contiguous to rear edge 34 and a front edge 221 that is immediately adjacent or contiguous to guard bar 28. According to some aspects, retaining element 50 can also be designed so that rear edge 219 is immediately adjacent or contiguous to guard bar 28, and front edge 221 is immediately adjacent or contiguous to rear edge 34. According to one aspect, rear and front edges 219, 221 are coplanar side surfaces of top portion 42, bottom portion 44 and intermediate portion 46.

Top portion 42 of retaining element 50 can be substantially planar and operable to abut each of the one or more blades 24 so that the one or more blades 24 can be secured in housing 30 of cartridge 22. Bottom portion 44 and intermediate portion 46 can be substantially rounded and, in coordination with top portion 42, and can be operable to substantially surround a portion of lateral surfaces YY of side edges 36, 38 of the housing 30. In short, intermediate portion 46 is positioned and substantially surrounds lateral surfaces YY while bottom portion 44 substantially surrounds undersurface 420 of housing 30. The curvature of bottom portion 44 can be defined by a plurality of radii inclusive of, for example, between 2 millimeters and 3 millimeters. However, according to other aspects, the curvature of bottom portion 44 is, for example, between 2.20 millimeters and 2.55 millimeters. The curvature of intermediate portion 46 can be defined by a plurality of radii, for example, between 1 millimeter and 6 millimeters. According to some aspects, intermediate portion 46 has a curvature, for example between 1.5 millimeters and 5.9 millimeters. In this aspect, upon installation of retaining element 50 onto side edges 36,38 of housing 30, top portion 42 of retaining element 50 can extend along an uppermost portion of side edges 36,38, and bottom portion 44 of retaining element 50 can be curved around a lowermost portion of side edges 36,38. According to other aspects, bottom portion 44 and/or intermediate portion 46 includes one or more straight portions along a length thereof and/or can include a single radius of curvature, without deviating from the scope of the present disclosure.

Retaining element 50 can have a thickness T that ranges throughout the length of retaining element 50, with the greatest thickness T, for example, being approximately 0.5 millimeters. Retaining element 50 can have a height H. Height H of retaining element 50 is measured from an uppermost surface 42a of top portion 42 to a lowermost surface 44b of bottom portion 44, and can be, for example, about 5.3 millimeters. Retaining element 50 also includes a distance f. Distance f is measured from first end 55 that is closest to a center 30a, as shown in FIG. 2, of housing 30 to a line tangent to the outer surface 215 of retaining element 50 that is farthest from the center of housing 30. In some examples, distance f can be about 4.0 millimeters. However, according to some aspects, the distance f ranges, for example, from about 3.0 millimeters to about 5.0 millimeters. An angle a is defined between a horizontal line 400 that is tangent to a lowermost point of bottom portion 44 and a line 402 that is tangent to an innermost point on the interior bottom surface 45 of bottom portion 44, can be, for example, approximately 22 degrees, when retaining element 50 is detached from the housing 30 of cartridge 22 and in an original or unloaded configuration. According to some aspects, the angle a can be a positive angle that can range from about 0 to about 60 degrees. The value of the angle a directly affects an ability of retaining element 50 to securely engage a specific housing 30 design, e.g., outer side 302. For instance, a decrease in the angle a results in a tighter engagement between the housing 30 and retaining element 50, and an increase in the angle a results in a looser engagement between the housing 30 and retaining element 50. Additionally, via the resilient nature of the material of retaining element 50, retaining element 50 can be designed so that the angle a is decreased when retaining element 50 is securely attached to the housing 30 of cartridge 22 or in a loaded configuration. Angle a can be, for example, between about 1 and 15 degrees.

Thus, to secure retaining element 50 to one of side edges 36, 38 of the housing 30, retaining element 50 can be flexibly expanded from the unloaded or original configuration when retaining element 50 is detached from the housing 30 of cartridge 22 and beyond the loaded configuration when retaining element 50 is securely attached to the housing 30 of cartridge 22, and is positioned and released so that the one of side edges 36, 38 is encompassed by the interior volume 48 of the retaining element 50. Upon release of retaining element 50, the resilient nature of the material of retaining element 50 causes retaining element 50 to resiliently return to its original configuration. The one of side edges 36, 38 prevents retaining element 50 from completely returning to the unloaded configuration and can cause bottom portion 44 of retaining element 50 to be displaced a distance r from the unloaded or original configuration when retaining element 50 is detached from the housing 30 of cartridge 22 and maintained in the loaded configuration when retaining element 50 is securely attached to the housing 30 of cartridge 22.

According to some aspects, the distance r is, for example, about 0.1 millimeter to about 0.3 millimeters. However, according to further aspects, the distance r is, for example, about 0.11 millimeters. In this manner, once retaining element 50 is installed on cartridge 22, the resilient nature of the material of retaining element 50 and the displacement by the distance r can cause retaining element 50 to apply a downward pressure on the one or more blades 24, so that the one or more blades 24 may be biased into the cartridge 22. The pressure applied by retaining element 50 can advantageously maintain the position of the one or more blades 24, thereby maintaining blade exposure of each of the one or more blades 24, with respect to a contact plane, and maintaining the required shaving angle values of cartridge 22 for an efficient shave. The contact plane refers to a plane that is formed on the surface of guard bar 28.

It should be appreciated by one of ordinary skill in the art that the dimensions and shapes of retaining element 50 are only an example of the present disclosure, a number of other dimensions and/or shapes can be used for retaining element 50. Such other shapes include, but are not limited to, triangular, oblong, square, rectangular, circular, semi-circular, elliptical, and other related shapes. It is foreseen that such other retaining element 50 designs can include same and/or similar components to retaining element 50, so as to be easily substituted in place of retaining element 50.

Retaining element 50 can connect to housing in alternative configurations, for example, as set forth in U.S. Patent Application Publication No. 2018/0361604 that is hereby incorporated by reference in its entirety.

Receiving portion 31 of housing includes a cavity 308 formed in top side 300. Lubricating composition 102 and pusher material 103 that form the shaving aid are positioned in cavity 308. Receiving portion 31 includes lubricating composition 102 and pusher material 103 that form the shaving aid of dispenser assembly 100. Retaining element 50 is connected to receiving portion 31 of housing 30.

FIG. 4A shows pusher material 103 forming a bottom layer relative to lubricating composition 102 which is a top layer. A portion of lubricating composition 102 is disposed in first aperture 51 and second aperture 52 of retaining element 50. During a shave, the lubricating composition wears and thereby releases the portion of lubricating composition 102. Pusher material 103, as shown in FIG. 4A, is a superabsorbent polymer. During a shave, the superabsorbent polymer of the bottom layer of pusher material 103 absorbs water and/or humidity and swells acting as a spring/pusher that pushes upwards on the top layer of lubricating composition 102 to release lubricants after being activated through contact with water through first aperture 51, second aperture 52, or both first aperture 51 and second aperture 52. Lubricating composition 102 can have a first portion 107 separated from a second portion 109 so that first portion 107 is dispensed through first aperture 51 and second portion 109 is dispensed through second aperture 52. Bottom layer that is pusher material 103 consisting of two sub-sections, first section 104 and second section 105. Second section 105 can form a groove 106 that is angled on opposite sides 106*a*, 106*b* so that side 106*a* directs first portion 107 outward away from bar 53 and side 106*b* directs second portion 109 outward away from bar 53 thereby exposing, respectively, first portion 107 and second portion 109 of lubricating composition 102 through first aperture 51 and second aperture 52 on top portion 42 of retaining element 50.

Figure 4B:
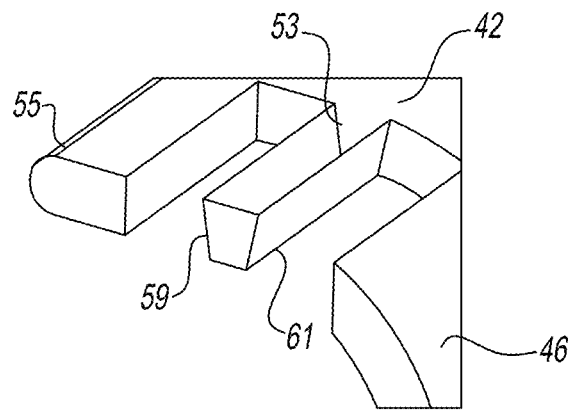
FIG. 4B is a partial cross-sectional view of the retaining element shown in FIG. 2 taken along line A-A showing an example of the bar and the draft angle.
Figure 4C:
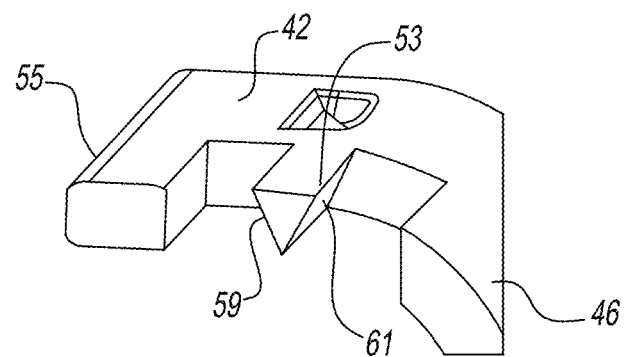
FIG. 4C is a partial cross-sectional view of the retaining element shown in FIG. 2 taken along line A-A showing another example of the bar and the draft angle.
Figure 4F:
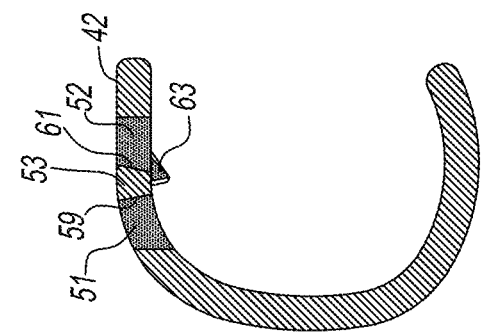
FIG. 4F is a side cross-sectional view of the retaining element of FIG. 4D taken along line B-B.
Figure 4E:
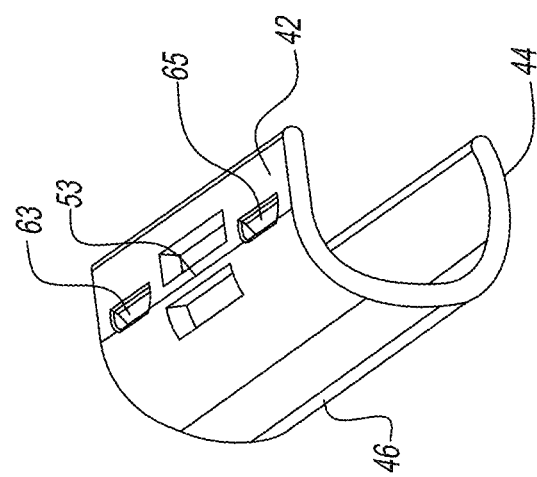
FIG. 4E is a side perspective view of the retaining element of FIG. 4D.
Figure 4D:
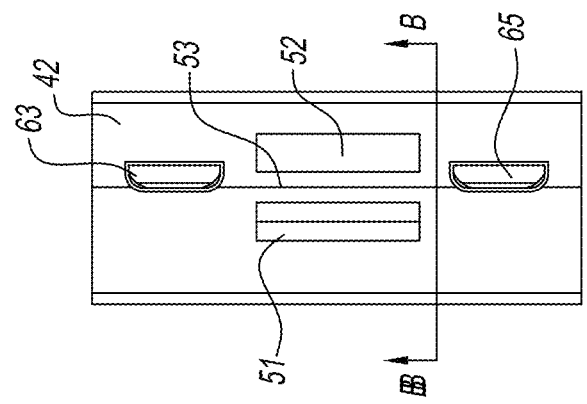
FIG. 4D is a top view of the retaining element of FIG. 3 that is modified to have locking projections.

Retaining element 50 can be produced through a stamping/forming process to form a C-shape with top portion 42, bottom portion 44 and intermediate portion 46 connecting the top portion 42 to the bottom portion 44. Top portion 42 includes a bar 53 extending lengthwise on top portion 42 of retaining element 50 and bar 53 divides first aperture 51 and second aperture 52, also extending lengthwise of the top portion 42 of retaining element 50. Bar 53 has opposing sides 59, 61. Sides 59, 61 form draft angles with planes 404*a*, 404*b*, respectively. Plane 404*a* forms a 90 degree angle with uppermost surface 42*a* of top portion 42. Plane 404*b* forms a 90 degree angle with uppermost surface 42*a* of top portion 42. Specifically, a first draft angle 406 is formed between plane 404*a* and side 59. A second draft angle 408 is formed between plane 404*b* and side 61. The first and second draft angles are produced during the stamping-forming process of retaining element 50. The configuration of first and second draft angles 406, 408 in the sides 59, 61 acts, additionally, as a friction barrier that controls the exposure of the shaving aid after swelling of the pusher material 103. It should also be noted that the larger the first and second draft angles 406, 408, the bigger the friction barrier. The first and second draft angles 406, 408 can range between 0-45 degrees. In some examples, the first and second draft angles 406, 408 can be 5-20 degrees. In other examples, as shown in FIG. 4B, the sides 59, 61 and the top portion 42 form a trapezoidal shape and the first and second draft angles 406, 408 can be approximately 10 degrees. Yet in another example, as shown in FIG. 4C, where the shape between the sides 59, 61 and the top portion 42 form a triangular shape, the first and second draft angles 406, 408 can be approximately 27 degrees. One or more holes 57 are formed through retaining element 50 from bottom interior surface 45 through the bottom portion 44, formed by applying punching method before the forming process. In some aspects, holes 57 can also be formed through intermediate portion 46, as long as holes 57 are able to communicate with pusher material 103 so as to allow the water to penetrate and induce swelling. Retaining element 50 can be modified to have a configuration shown in FIGS. 4D-4F wherein instead of utilizing projection 56 to couple the retaining element 50 to the housing 30, bar 53 of the retaining element 50 can include locking projections 63 and 65 to facilitate coupling the retaining element 50 to the housing 30.

Housing 30 of the cartridge 22 can be produced through injection molding with cavity 308 in place and retaining elements 50 are incorporated on both side edges 36 and 38 of the housing 30 to enclose cavity 308. Retaining elements 50 are incorporated on both side edges 36 and 38 such that intermediate portion 46 is positioned and substantially surrounds lateral surfaces YY while bottom portion 44 substantially surrounds undersurface 420 of housing 30. Injection molding of housing 30 can also produce holes 37 formed from cavity 308 to an exterior bottom surface 39 of housing 30. Cavity 308 of housing 30 accommodates the shaving aid. As such, and as noted above, through an action of bottom layer that is pusher material 103 coming in contact with water, a top portion of lubricating composition 102 is able to be exposed through first aperture 51 and second aperture 52 on top portion 42 of retaining element 50.

Lubricating composition 102 and pusher material 103 of the shaving aid can be incorporated into cavity 308 of housing 30 via press-fit method. Cavity 308 of housing 30 is configured in the shape of lubricating composition 102 and pusher material 103 of the shaving aid, such that lubricating composition 102 and pusher material 103 of the shaving aid can be hosted in housing 30. Lubricating composition 102 and pusher material 103 are kept in place in cavity 308 of housing 30 due to bar 53 acting as a barrier on top portion 42 of retaining element 50.

As noted, the shaving aid consists of two layers: lubricating composition 102 and pusher material 103. The bottom layer that is pusher material 103 includes a superabsorbent composition, which is divided in two sub-sections, first section 104 and second section 105. Pusher material 103 can be formed by a cutting tool. Pusher material 103 that forms the bottom layer plays the role of the spring/pusher because first section 104 that is the lower sub-section swells in contact with water. During wet shaving, water penetrates into housing 30 to activate first section 104 of the bottom layer of the shaving aid causing the first section 104 to swell. Penetration of water through the first section 104 occurs via holes 57 formed in the bottom portion of retaining element 50 and holes 37 of housing 30, wherein the holes 37 are provided in fluid communication with the holes 57 provided in the bottom portion 44 of the retainer 50. In other words, the holes 37 are configured to match the holes 57 provided in the bottom portion 44 of the retainer 50. In some examples, holes 37 can also be formed through receiving portion 31 of housing 30 and holes 57 can for formed through intermediate portion 46 of retaining element 50, where holes 37 and 57 match and are in fluid communication.

The superabsorbent composition of pusher material 103 can include a base polymer or copolymer that forms second section 105, for example, polymer or copolymer consisting of amide and ether groups, e.g. polyether block amides and, a hydrophilic coating grafted therein that forms first section 104. The hydrophilic coating of first section 104 can be a polymer resulting from a vinyl monomer with hydrophilic properties, such as acrylic acid, acrylamide or polyvinyl alcohol that is grafted on the surface of the polymer base of second section 105, which is already activated so as to have functional groups for bonding with the vinyl monomer. The vinyl monomer, such as acrylic acid, acrylamide, polyvinyl alcohol is then polymerized to create the polymer coating, which is hydrophilic. In other examples, the second section 105 of the pusher material 103 may further include a thermoplastic elastomer material, e.g. thermoplastic polyurethane (TPU), additional to the aforementioned base polymer or copolymer. The thermoplastic elastomer material may constitute the core ingredient of the second section 105 and the base polymer or copolymer may be added as a single layer in at least one outer surface of the second section 105, where the outer surface(s) of the second section 105 define(s) the area between the second section 105 and the first section 104 and the area between the second portion 105 and the lubricating composition 102. As such, the hydrophilic coating may be grafted to any outer surface of the second section 105, while the hydrophilic coating constitutes the first section 104 and/or the lubricating composition 102. An example of superabsorbent composition and its manufacturing is disclosed in the European Patent No. EP2576673 that is hereby incorporated by reference in its entirety.

Lubricating composition 102, which is the top layer, is a lubricious composition being a mixture of water-soluble and water-insoluble ingredients that retains the same shape when in contact with water to thereby provide lubrication. The lubricating composition 102 provides lubrication while retaining the shape of the shaving aid, because the lubricating composition 102 is not eroded superficially, but the water-soluble ingredients contained therein are released from the lubricating composition 102 in bulk. In some aspects, lubricating composition 102 that is the top layer can be of the same material as the first section 104. In those aspects, lubricating composition 102, which is the top layer, provides glideness.

The lubricious composition includes, fundamentally, a water-soluble material (e.g., polyethylene oxide generally known as POLYOX or ALKOX) and a water-insoluble material (e.g. high impact polystyrene). Examples of rigid water-insoluble components are polystyrene, styrene co-polymers, polyethylene, polypropylene, polyacetal, acrylonitrile-butadiene-styrene copolymer, ethylene vinyl acetal copolymer, polylactic acid, polycarbonate, maleic anhydride ethylene co-polymer blends, polyether-containing block copolymers (e.g. with polyamide), blends and copolymers of the above with or without other additives. Examples of elastic water-insoluble components are thermoplastic elastomer compounds (TPEs), more specifically thermoplastic poly-urethanes, and/or silicone polymers. Typical examples of water-soluble components are polyethylene oxide and/or polyethylene glycol, polyvinyl pyrrolidone, polyacrylamide, polyhydroxymethacrylate, polyvinyl imidazoline, polyvinyl alcohol, polyhydromethymethacrylate, silicone polymers, blends and copolymers of the above. The lubricious composition can additionally contain other ingredients selected from the group of plasticizers, such as low molecular weight polyethylene glycols, water-swellable release enhancing agents, such as cross-linked polyacrylics and/or maleic anhydride compounds, additional lubricants, compatibilizers, and/or skin care agents selected from the group consisting of vitamins, botanical extracts, salts, humectants, silicon oils, organic oils, waxes, antioxidants, exfoliants, anti-bacterial agents, anti-microbial, antiseptics, biocides, preservatives, skin soothing agents, hydrating agents, skin protectants, colorants, film formers, processing thickening agents from the list of silica, fume silica, TiO2 particles, and combinations thereof.

A different lubricious composition of lubricating composition 102 can be provided in each of the first aperture 51 and the second aperture 52 formed in the top portion 42 of retaining element 50, especially where the lubricious composition includes different cosmetic ingredients to offer several skin care benefits.

Lubricating composition 102 can include additional ingredients such as, for example, one or more emulsifiers, surfactants, skin conditioners, fragrances, depilatory agents, cleaning agents, medicinal agents. In some examples, additional ingredients can include mineral oil; cooling agents; anti-irritation agents such as a pyrithione or a polyvalent metal salt of pyrithione; moisturizing agents selected from olive oil, jojoba oil and glycerin; and/or essential oil materials, such as menthol, eugenol, eucalyptol, saffrol or methyl salicylate.

When lubricating composition 102 is the top layer, the lubricious composition can be formed via extrusion. However, when lubricating composition 102 is the top layer, and includes a superabsorbent composition, and pusher material 103 is the bottom layer and is a superabsorbent composition, the superabsorbent composition of pusher material 103 can be produced in two stages. Namely, the base polymer can be formed via injection and then the hydrophilic coating can be formed on the base polymer according to the manufacturing process described in European Patent No. EP2576673 that is hereby incorporated by reference in its entirety. The two layers, lubricating composition 102 and pusher material 103, form the shaving aid and are attached to each other through adhesion. Subsequently, lubricating composition 102 and pusher material 103 of the shaving aid, are incorporated in housing 30, prior to the incorporation of the one or more blades 24, in a linear assembly machine. Lubricating composition 102 and pusher material 103 are locked in cavity 308 of the housing 30 by bar 53 that is located in top portion 42 of retaining element 50. Bar 53 is configured to lock lubricating composition 102 and pusher material 103 in position within the cavity 308. An alternative that is not shown can include inner surface of bar 53 that can be shaped as a locking projection for retaining element 50 to be assembled/engaged with housing 30, for example, housing 30 can form portions on opposite ends of bar 53 that are inserted in first aperture 51 and second aperture 52 to mate with sides 59, 61, respectively, engaging housing 30 with bar 53. After incorporation of lubricating composition 102 and pusher material 103 in cavity 308 of housing 30, retaining elements 50 are assembled/engaged with housing 30 by snap-fit, so as to act as a "lid" and envelope the shaving aid. Particularly, each retaining element 50, being C-shaped in configuration, is formed to be snap-fitted onto housing 30 through locking projection(s) 56 or 63 and 65 that is(are) anchored in complementary apertures or grooves similar to grooves 306 of housing 30.

In some embodiments, a single dispenser assembly 100 can be disposed on only one side of the housing 30. However, in other embodiments, as shown in FIGS. 1 and 2, a single dispenser assembly 100 can be disposed on each side of housing 30 where side edge 36 also has a receiving portion 33 that has a shape that is a mirror image of receiving portion 31 that mates with another or second retaining element 50.

Razor cartridges with an aluminum retaining element such as retaining element 50 serving to retain one or more blades 24 can have, for example, an interior volume 48 of approximately 50 mm$^3$ to 130 mm$^3$ that is available on each of the left and right sides 36, 38 of the housing 30 where lubricating composition 102 can be positioned. Thus, it is also perceived that according to other aspects, the available interior volume 48 can be replaced by a suitably sized container having varying shapes and sizes so as to adapt to the available interior volume 48.

Referring again to FIGS. 1 and 2, housing 30 can include an optional lubricating strip 26 adjacent to rear edge 34 for lubricating the skin, and a skin shield or guard bar 28 arranged proximate to front edge 32 and between the pair of side edges 36, 38 to protect the user from injuries such as, for example, injuries that may be due to direct contact of the skin with the leading blade edge. Additionally, guard bar 28 can stretch the skin for better shaving performance.

Although the housing 30 of FIGS. 1 and 2 is illustrated with five razor blades 24, any number of blades can be used, inclusive of the use of a single blade. Accordingly, the cavity 308 of the housing 30 which hosts the shaving aid would be adjusted depending upon the number of blades disposed in the housing 30.

According to some aspects, the present disclosure also provides for the use of additional shaving aids, namely, dispenser assembly 100 can be in a razor housing to cooperate with other shaving aids such as, for example, lubricating strips and guard bars. The use of additional shaving aids can extend the lifetime of razor 10.

Dispenser assembly 100 improves lubricity and glideness of razor 10 during shaving by exploiting existing components of razor 10, without need for additional accessories, i.e. external components. Lubricating composition 102 of the shaving aid, which is disposed in cavity 308 of housing 30 and captured by interior volume 48 of retaining element 50, is released so as to provide lubrication when in contact with the skin of a user. Lubricating composition 102 and pusher material 103, which together form the shaving aid, are incorporated into cavity 308 that is formed in the side edges 36, 38 of housing 30 and assembled to engage with interior volume 48 of retaining element 50. Particularly, lubricating composition 102 and pusher material 103 are incorporated within cavity 308 of the housing 30 and encompassed by interior volume 48 of the C-shaped retaining elements 50.

Figure 5:
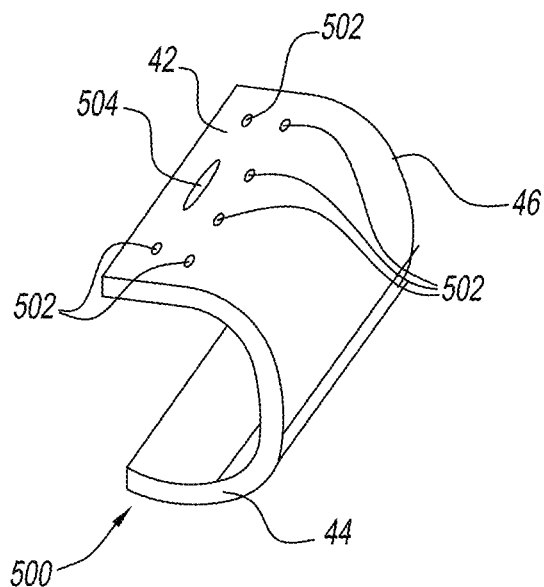
FIG. 5 is a side perspective view of another retaining element having a hole pattern for a second cartridge that is modified from the cartridge shown in FIG. 2.

Referring to FIG. 5, another retaining element 500 is shown. Retaining element 500 is the same as retaining element 50 except retaining element 500 has holes 502 in top portion 42 instead of having a first aperture 51, second aperture 52 and bar 53. Lubrication composition 102, disposed in housing 30, is released through holes 502 of retaining element 500. Retaining element 500 does not include hole 57 formed in bottom portion 44. Retaining element 500 also has a projection 508 (FIG. 7) created by locking feature 504 formed in top portion 42. Locking feature 504 can have the same or a different shape than projection 56, 508.

Figure 6:
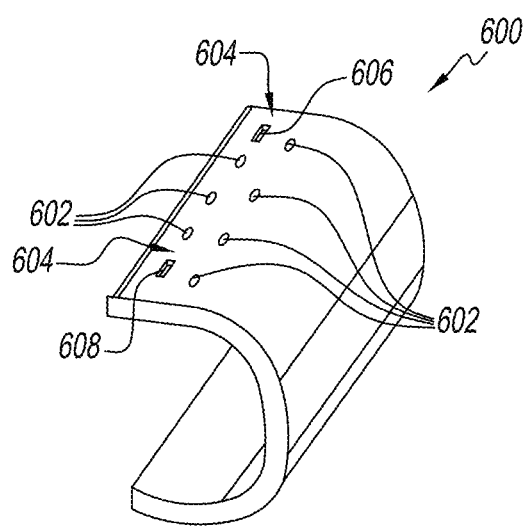
FIG. 6 is a side perspective view of a retaining element having a second hole pattern different from the hole pattern of FIG. 5 that can used with the second cartridge.

Referring to FIG. 6, another retaining element 600 is shown that is the same as retaining element 500 except retaining element 600 has holes 602 formed in a different pattern than holes 502. Lubrication composition 102, disposed in housing 30, is released through holes 602. Further, retaining element 600 has locking feature 604 that consists of a pair of locking elements 606 and 608 instead of the one locking feature 504 of retaining element 500.

Figure 7:
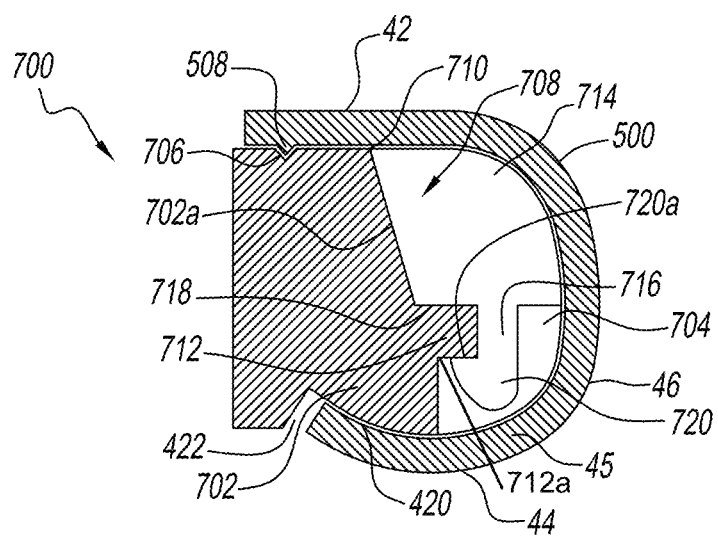
FIG. 7 is a side, cross-sectional view of a portion of the second cartridge having the retaining element of FIG. 5.

Referring to FIG. 7, retaining element 500 is connected to a housing 702 of razor 700. Alternatively, retaining element 600 can be connected to razor 700 instead of retaining element 500. Razor 700 is the same as razor 10 except housing 702 is provided with a cavity 704 that has a different shape than cavity 308 of housing 30. Also, housing 702 can have the same or a different shape groove 706 than groove 306 of housing 30. Ultimately, groove 706 should complement or correspond to the shape of projection 508.

Retaining element 500 can be produced through a stamping/forming process where a flat strip/sheet of metal material, such as for example aluminum, is stamped/formed into a C-shape about the cavity 704 of the housing 702. C-shaped retaining element 500 also includes a top portion 42, bottom portion 44 and an intermediate portion 46 connecting the top portion 42 to the bottom portion 44. Top portion 42 includes one or more therethrough holes 502. In one example, there are no more than two holes 502, or one elongated aperture can form hole 502. Holes 502 can be formed by applying a punching method before the stamping/forming process.

Housing 702 of razor 700 can be produced through injection molding or gravity molding with cavity 704 being formed in a place and retaining elements 500 are incorporated on both side edges 36 and 38 of the housing 702 to enclose cavity 704. Retaining elements 500 are incorporated on both side edges 36 and 38 such that intermediate portion 46 is positioned and substantially surrounds lateral surfaces YY while bottom portion 44 substantially surrounds undersurface 420 of housing 702. Cavity 704 of housing 702 accommodates a shaving aid 708 instead of the lubricating composition 102 and pusher material 103 of other examples. Shaving aid 708, which is disposed in cavity 704 of housing 702 is captured by interior volume 48 of retaining element 500 and is released through retaining element 500 so as to provide lubrication when in contact with the skin of a user. Cavity 704 is defined between the top interior surface 43 of top portion 42 and the interior bottom surface 45 of bottom portion 44 of each retaining element 500, when the retaining element 500 is installed about the housing 702.

Figure 8:
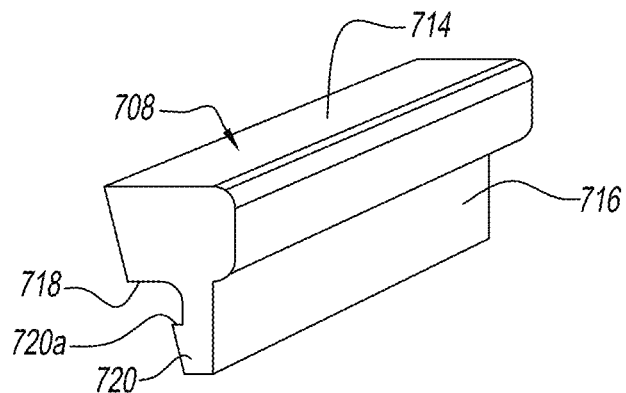
FIG. 8 is a side perspective view of a shaving aid of the cartridge of FIG. 7.
Figure 9:
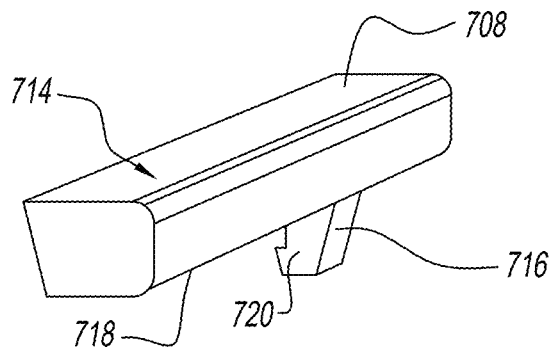
FIG. 9 is a side perspective view of a shaving aid having a modified shape from that shown in FIG. 8 for use with the second cartridge.

Shaving aid 708 includes a main body 714 and a protrusion 716 extending from a bottom surface 718 of the main body 714. Particularly, protrusion 716 includes a lip 720 and is designed as a hook, to act as a snapping feature for when the shaving aid 708 is incorporated into the cavity 704 of housing 702. Housing 702 further includes an abutment 712 that projects outwardly from an outer surface 702a. Shaving aid 708 can be incorporated into cavity 704 of housing 702 such as by snap-fit method. Thus, upon insertion of the shaving aid 708 into cavity 704 of housing 702, lip 720 interacts with the abutment 712 and is snap-fitted under abutment 712 such that an upper surface 720a of lip 720 engages a lower surface 712a of abutment 712. Main body 714 of the shaving aid 708 is configured in a shape so as to be hosted in the cavity 704 to abut with the outer surface 702a of the housing and to conform with the shape of the retaining element 500. Shaving aid 708 can have one or more protrusions 716 shaped as hooks, dispersed in one or several positions along bottom surface 718 of shaving aid 708, as shown in FIG. 9, or shaving aid 708 can have one elongated protrusion 716 shaped as continuous hook that extends uniformly along bottom surface 718 of shaving aid 708, as shown in FIG. 8.

Figure 18:
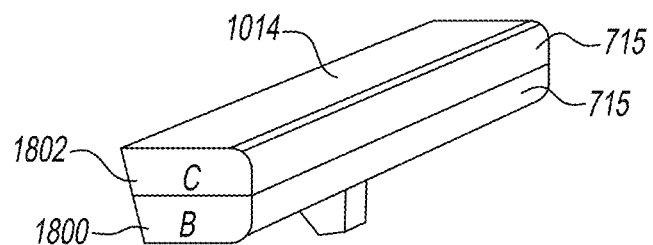
FIG. 18 is a side perspective view of a shaving aid having a modified material from that shown in FIG. 17 for use with the third cartridge.

Shaving aid 708 can be produced through extrusion or injection. When the mechanical properties of protrusions 716 are not suitable for the extrusion or injection processes, such as for instance, where a solid engagement of shaving aid 708 is not allowed in cavity 704, protrusions 716 and main body 714 of shaving aid 708 may each be formed separately and produced from different materials and joined together by applying co-injection or co-extrusion processes, as shown in FIG. 18 and detailed further below.

Figure 10:
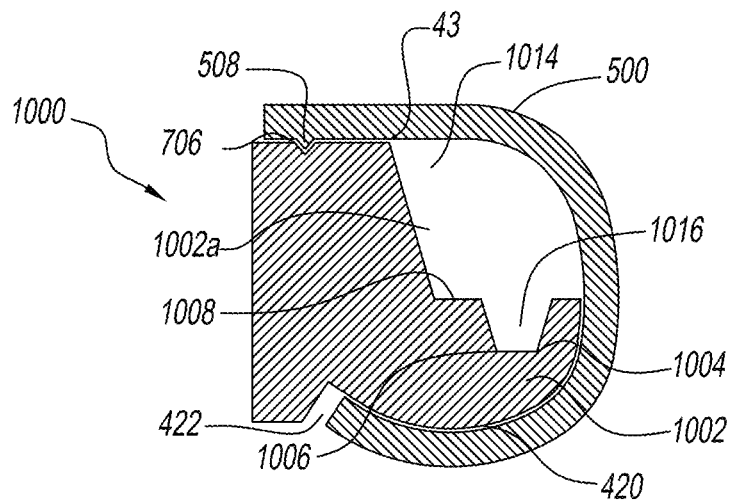
FIG. 10 is a side, cross-sectional view of a portion of a third cartridge that is modified from the cartridge shown in FIG. 2 having the retaining element of FIG. 5 and the shaving aid removed.
Figure 11:
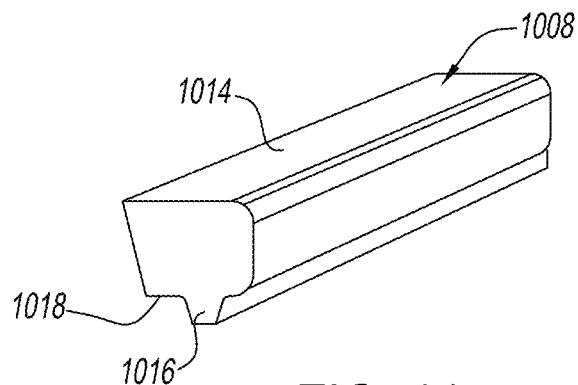
FIG. 11 is a side perspective view of a shaving aid of the third cartridge of FIG. 10.
Figure 12:
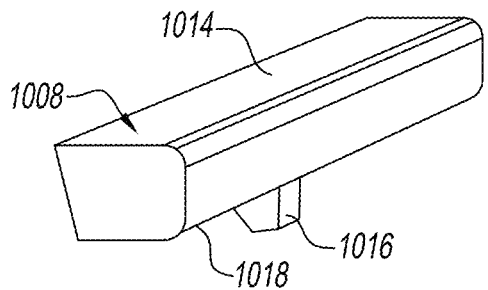
FIG. 12 is a side perspective view of a shaving aid having a modified shape from FIG. 11 for use with the third cartridge of FIG. 10.

Referring to FIGS. 10-12, retaining element 500 is connected to a razor 1000. Razor 1000 is the same as razor 700 except razor 1000 has a housing 1002 with a cavity 1004 having a different shape than cavity 704 of housing 702. Housing 1002 can also have the same or a different shape groove 706 than groove 306 of housing 30. As with housing 702, ultimately, groove 706 should complement or correspond to the shape of projection 508.

Housing 1002 of razor 1000 can be produced through injection molding or gravity molding with cavity 1004 being formed in place and retaining elements 500 are incorporated on both side edges 36 and 38 of the housing 1002 to enclose cavity 1004. Retaining elements 500 are incorporated on both side edges 36 and 38 such that intermediate portion 46 is positioned and substantially surrounds lateral surfaces YY while bottom portion 44 substantially surrounds undersurface 420 of housing 1002. During the injection molding or gravity molding process, a groove 1006 is further formed in the housing 1002. Cavity 1004 of housing 1002 accommodates a shaving aid 1008 instead of the lubricating composition 102 and pusher material 103 of other examples. Shaving aid 1008, which is disposed in cavity 1004 of housing 1002 is captured by interior volume 48 of retaining element 500 and is released through retaining element 500 so as to provide lubrication when in contact with the skin of a user. Cavity 1004 is defined between the top interior surface 43 of the top portion 42 and a bottom surface of the groove 1006, when the retaining element 500 is installed about the housing 1002.

Shaving aid 1008 includes a main body 1014 and a protrusion 1016 extending from a bottom surface 1018 of the main body 1014. The shape of the protrusion 1016 is complementary to a shape of the groove 1006. As such, the protrusion 1016 acts as a locking feature and allows the shaving aid 1008 to be fixed or wedged in the groove 1006. Main body 1014 of the shaving aid 1008 is configured in shape so as to be hosted in the cavity 1004 to abut with an outer surface 1002a of the housing and to conform with the shape of the retaining element 500. Thus, shaving aid 1008 can be inserted into cavity 1004 by press-fit method where protrusion 1016 engages with groove 1006 and locks the shaving aid 1008 within the cavity 1004 of housing 1002.

In other embodiments, shaving aid 1008 can include one or more protrusions 1016, dispersed in one or several positions along bottom surface 1018 of shaving aid 1008, as shown in FIG. 12, or shaving aid 1008 can include one continuous elongated protrusion 1016 that extends uniformly along bottom surface 1018 of shaving aid 1008, as shown in FIG. 11. Main body 1014 and the one or more protrusions 1016 of shaving aid 1008 can be produced through extrusion or injection. When the mechanical properties of the protrusions 1016 are not suitable for the extrusion or injection process, such as for instance, to allow for a solid engagement of shaving aid 1008 in cavity 1004, protrusions 1016 and main body 1014 of shaving aid 1008 can be each formed separately and produced from different materials and joined together by applying co-injection or co-extrusion processes, as shown in FIG. 18 and detailed further below.

Figure 13:
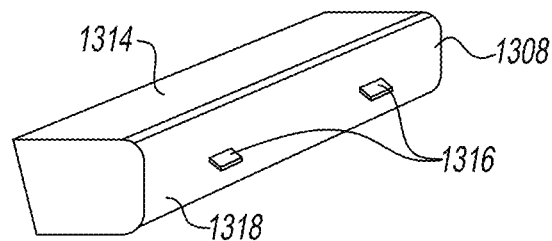
FIG. 13 is a side perspective view of a shaving aid of a fourth cartridge that is modified from the cartridge shown in FIG. 2 having the retaining element of FIG. 5.

Referring to FIG. 13, another shaving aid 1308 is shown that is similar to shaving aid 1008 except shaving aid 1308 can be incorporated into the cavity 1004 of the housing 1002 of razor 1000 by ultrasonic welding. In this embodiment, the volume of the cavity 1004 accommodates shaving aid 1308 instead of shaving aid 1008.

Shaving aid 1308 includes a main body 1314 and one or more protrusions 1316 extending from a bottom surface 1318 of the main body 1314. The protrusions 1316 are formed from a material that is capable of melting and being welded by applying ultrasonic vibration. As such, the protrusions 1316 act as energy directors that upon being melted and welded keep the shaving aid 1318 locked within the cavity 1004 of the housing 1002. The energy directors formed by protrusions 1316 can be made with materials that are compatible with the material of the housing 1002. The main body 1314 and protrusions 1316 can be produced through injection molding.

Figure 14:
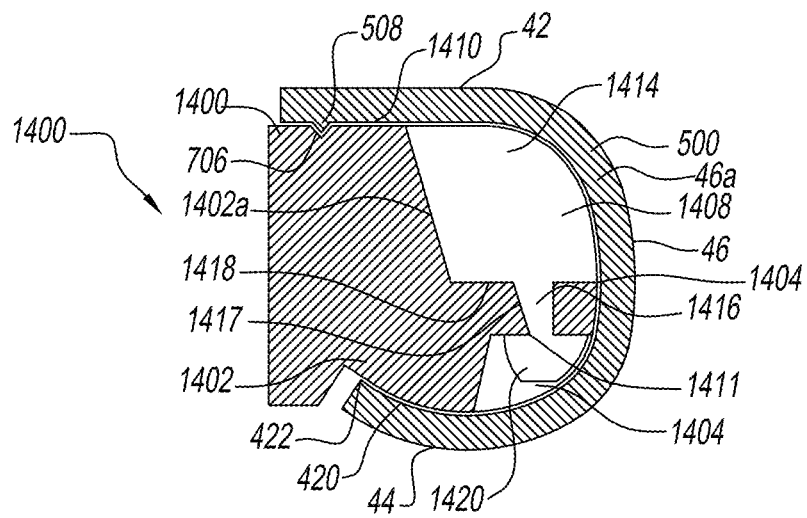
FIG. 14 is a side, cross-sectional view of a portion of a fifth cartridge that is modified from the cartridge shown in FIG. 2 having the retaining element of FIG. 5.
Figure 15:
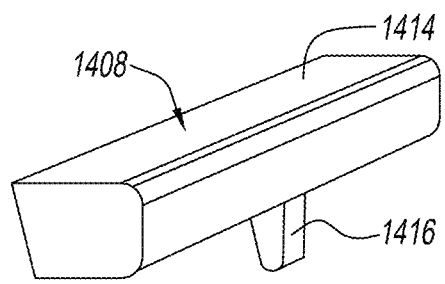
FIG. 15 is a side perspective view of a shaving aid of the fifth cartridge of FIG. 14.

Referring to FIGS. 14 and 15, retaining element 500 is connected to a razor 1400. Razor 1400 is the same as razor 700 and 1000 except razor 1400 includes a housing 1402 with a cavity 1404 having a different shape than cavities 704 and 1004 of housings 702 and 1002, respectively. Housing 1402 can also have the same or a different shape groove 706 than groove 306 of housing 30. As with housings 702 and 1002, ultimately, groove 706 should complement or correspond to the shape of projection 508.

Housing 1402 of razor 1400 can be produced through injection molding or gravity molding with cavity 1404 being formed in place and retaining elements 500 are incorporated on both side edges 36 and 38 of the housing 1402 to enclose cavity 1404. Retaining elements 500 are incorporated on both side edges 36 and 38 such that intermediate portion 46 is positioned and substantially surrounds lateral surfaces YY while bottom portion 44 substantially surrounds undersurface 420 of housing 1402. Cavity 1404 of housing 1402 accommodates a shaving aid 1408 instead of the lubricating composition 102 and pusher material 103 of other examples. Shaving aid 1408, which is disposed in cavity 1404 of housing 1402 is captured by interior volume 48 of retaining element 500 and is released through retaining element 500 so as to provide lubrication when in contact with the skin of a user. Cavity 1404 is defined between the top interior surface 43 of the top portion 42 and an interior bottom surface 45 of the bottom portion 44, when the retaining element 500 is installed about the housing 1402. Cavity 1404 is designed specifically to accommodate a shaving aid 1408 instead of the lubricating composition 102 and pusher material 103 that form the shaving aid in previous examples.

Shaving aid 1408 includes a main body 1414 having a shaft 1416 extending from a bottom surface 1418 of the main body 1414. Shaft 1416 includes a fastening feature 1420 disposed at an end thereof. An arm 1411 extends from an outer surface 1402a of housing 1402. Arm 1411 extends from the outer surface 1402a of the housing 1402 to interior surface 46a of intermediate portion 46. Arm 1411 includes an opening 1417 for receipt of shaft 1416 and fastening feature 1420. Thus, shaving aid 1408 can be incorporated into cavity 1404 of housing 1402 by, for example, riveting where fastening feature 1420 interacts with arm 1411 to lock shaving aid 1408 within in cavity 1404. In this embodiment, the shaft 1416 is particularly designed to be tightly assembled/engaged with opening 1417 formed in arm 1411. As such, shaft 1416 which is larger than opening 1417 and is undeformed, as shown in FIG. 15, passes through opening 1417 in arm 1411 where and end region of shaft 1416 deforms as it exits opening 1417 thereby forming fastening feature 1420 on an underside of arm 1411. Fastening feature 1420, after exiting opening 1417 and now being larger than opening 1417 maintains shaving aid 1408 in place within cavity 1404. Main body 1414 and shaft 1416 can be produced through injection.

Figure 16:
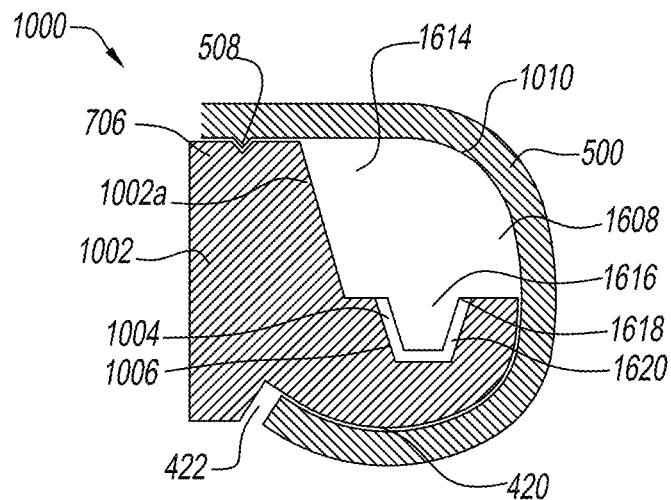
FIG. 16 is a side perspective view of the third cartridge having a shaving aid with a modified shape from that shown in FIG. 10.

Referring to FIG. 16, a shaving aid 1608 can be inserted or incorporated to cavity 1004 in housing 1002 of FIG. 10 via a loose-fit method. This method is an alternative of the press-fit method of FIG. 10.

In the loose-fit method, the shaving aid 1608 also includes a main body 1614 and a continuous elongated protrusion 1616 that extends uniformly along a bottom surface 1618 of the main body 1614. Protrusion 1616 has a shape that is complementary to the shape of groove 1006; however, protrusion 1616 is slightly smaller in size than groove 1006. As such, a gap 1620 is formed between protrusion 1616 and housing 1002 thereby creating a loose-fitting connection of the shaving aid 1608 within the housing 1002. During assembly of the razor 1000, shaving aid 1608 is kept in place by a conveyor belt of an assembly machine wherein the conveyor belt maintains a position of shaving aid 1608 within groove 1006 until the end of the assembly process when the retaining element 500 is installed thereby locking the shaving aid 1608 in razor 1000. Thereafter, retaining elements 500 are incorporated on both side edges 36 and 38 of the housing 1002 to enclose cavity 1004. Retaining elements 500 are incorporated on both side edges 36 and 38 such that intermediate portion 46 is positioned and substantially surrounds lateral surfaces YY while bottom portion 44 substantially surrounds undersurface 420 of housing 1002. Cavity 1004 of housing 1002 accommodates a shaving aid 1608 instead of the lubricating composition 102 and pusher material 103 of other examples. Shaving aid 1608, which is disposed in cavity 1004 of housing 1002 is captured by interior volume 48 of retaining element 500 and is released through retaining element 500 so as to provide lubrication when in contact with the skin of a user.

In other embodiments, shaving aid 1608 can include one or more protrusions 1616 dispersed in several positions along bottom surface 1618. In either embodiment, the main body 1614 and the one or more protrusions 1616 can be produced together or can each be produced separately through extrusion or injection molding. Should the mechanical properties of protrusions 1616 not be suitable to allow for a solid engagement of shaving aid 1608 within cavity 1004, protrusions 1616 and main body 1614 of shaving aid 1608 can, instead, not only be made separately but can also be made from different materials by applying co-injection, overmolding or co-extrusion processes. Co-injection, overmolding or co-extrusion processes discussed herein can be, for example, co-injection, overmolding or co-extrusion processes that are known in the art.

After incorporation of shaving aids 708, 1008, 1308, 1408, 1608 into the cavity, for example, cavity 704, 1004, 1404, the retaining elements 500, 600 are assembled/engaged with the housing, using snap-fit methodology. Particularly, retaining elements 500, 600 in C-shape form a snap-fit on at least a portion of a side edge 36, 38 of the housing 30, through projections 508 which are locking projections and are configured to anchor in a complementary groove 706 of the housing 30, for example, housings 702, 1002, 1402. Housing 30 includes undersurface 420 and is molded with indent 422 whereby indent 422 is shaped to receive bottom portion 44 of retaining element 50 and secure shaving aids 708, 1008, 1308, 1408, 1608 into the cavities 704, 1004, 1404.

Projection 508 can be two projections located on two positions on top portion 42 of retaining element 600, as shown in FIG. 6, for saving space for holes 602, or there are locking projections at only one location in a middle of top portion 42 of retaining element 500, as shown in FIG. 5.

Shaving aid 708, 1008, 1308, 1408, 1608 is in solid form and comprises main body 714, 1014, 1314, 1414, 1614, respectively, and one or more protrusions 716, 1016, 1316, 1416, 1616, respectively. Shaving aid 708, 1008, 1308, 1408, 1608 can be produced by gravity injection molding, extrusion or injection molding. Shaving aid 708, 1008, 1308, 1408, 1608 can also be produced by co-extrusion or co-injection should their respective protrusions 716, 1016, 1316, 1416, 1616 be made of material with low mechanical properties. Main body 714, 1014, 1314, 1414, 1614 and its respective protrusions 716, 1016, 1316, 1416, 1616 can be made with the same material or different material.

Shaving aid 708, 1008, 1308, 1408, 1608 is incorporated in housing prior to the incorporation of the one or more blades 24, in a linear assembly machine. Shaving aid 708, 1008, 1308, 1408, 1608 is locked within the cavity 704, 1004, 1404 of the housing 502, 702, 1002, 1402 thereby filling the inner volume created between the outer surface of the housing 502, 702, 1002, 1402 and the retaining elements 500, 600. According to a formula used for the shaving aid 708, 1008, 1308, 1408, 1608, each shaving aid 708, 1008, 1308, 1408, 1608 is water-activated to contribute lubrication and/or swells to contribute glideness when coming in contact with water. Top portion 42 of retaining element 500, 600 includes holes 502, 602 formed therethrough that allow water during a wet shave to seep through holes 502, 602 and make in contact with shaving aid 708, 1008, 1308, 1408, 1608.

The formulations of shaving aid 708, 1008, 1308, 1408, 1608, can be a lubricious composition that fundamentally includes a water-soluble material (e.g., polyethylene oxide generally known as POLYOX or ALKOX) and a water-insoluble material (e.g. high impact polystyrene). When a lubricious composition is used, shaving aid 708, 1008, 1308, 1408, 1608 requires water to be activated and to contribute lubrication.

Examples of rigid water-insoluble material are polystyrene, styrene co-polymers, polyethylene, polypropylene, polyacetal, acrylonitrile-butadiene-styrene copolymer, ethylene vinyl acetal copolymer, polylactic acid, polycarbonate, maleic anhydride ethylene co-polymer blends, polyether-containing block copolymers (e.g. with polyamide), blends and copolymers of the above with or without other additives. Examples of elastic water-insoluble components are thermoplastic elastomer compounds (TPEs), more specifically thermoplastic poly-urethanes, and/or silicone polymers. Typical examples of water-soluble components are polyethylene oxide and/or polyethylene glycol, polyvinyl pyrrolidone, polyacrylamide, polyhydroxymethacrylate, polyvinyl imidazoline, polyvinyl alcohol, polyhydromethymethacrylate, silicone polymers, blends and copolymers of the above. The lubricious composition can additional contain other ingredients selected in the group of plasticizers, such as low molecular weight polyethylene glycols, water-swellable release enhancing agents, such as cross-linked polyacrylics and/or maleic anhydride compounds, additional lubricants, compatibilizers, and/or skin care agents selected in the group consisting of vitamins, botanical extracts, salts, humectants, silicon oils, organic oils, waxes, antioxidants, exfoliants, anti-bacterial agents, anti-microbial, antiseptics, biocides, preservatives, skin soothing agents, hydrating agents, skin protectants, colorants, film formers, processing thickening agents from the list of silica, fume silica, TiO2 particles, and combinations thereof.

Figure 17:
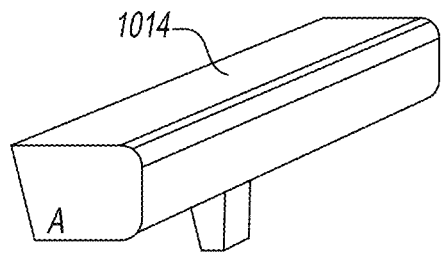
FIG. 17 is a side perspective view of a shaving aid for the third cartridge.

In some examples, main body 714, 1014, 1314, 1414, 1614 can be configured as a single, unique composition A, for example, main body 1014 as shown in FIG. 17, or can be structured in two or more layers 715, having two different and unique compositions B, C, for example, main body 1014 as shown in FIG. 18.

In examples that main body 714, 1014, 1314, 1414, 1614 is structured in two or more layers 715 in FIG. 18, each layer can include a different lubricious composition, containing different cosmetic ingredients to offer different skin care benefits as detailed above.

In other embodiments, when the main body 714, 1014, 1314, 1414, 1614 is structured in two or more layers 715. The two or more layers 715 can include a water-insoluble material (e.g. high impact polystyrene or thermoplastic elastomer) as bottom layer 1800 and a hydrophilic composition as top layer 1802. In these embodiments, the hydrophilic composition can be a lubricious composition as described above. In other embodiments, the hydrophilic composition can be a superabsorbent composition that comprises a base polymer or copolymer, for example, polymer or copolymer consisting of amide and ether groups, e.g. polyether block amides, with a hydrophilic coating grafted therein. In other examples, the hydrophilic composition may be a superabsorbent composition that comprises a thermoplastic elastomer material, e.g. thermoplastic polyurethane (TPU), additional to the aforementioned base polymer or copolymer, wherein the base polymer or copolymer is located on top of the thermoplastic elastomer material and the hydrophilic coating is grafted onto the base polymer or copolymer. The hydrophilic coating can be a polymer resulting from a vinyl monomer with hydrophilic properties, such as acrylic acid, acrylamide or polyvinyl alcohol that is grafted on the surface of the polymer base, which is already activated so as to have functional groups for bonding with the vinyl monomer. The vinyl monomer, such as acrylic acid, acrylamide, polyvinyl alcohol is then polymerized to create the polymer coating, which is hydrophilic. An example of superabsorbent composition and its manufacturing is disclosed in the European Patent No. EP2576673 that is hereby incorporated by reference in its entirety. When a superabsorbent composition is used as shaving aid, the shaving aid can swell when in contact with water and can contribute glideness.

Shaving aid 102, 103, 708, 1008, 1308, 1408, 1608 is only incorporated during the assembly of retaining elements 50, 500, 600 to housing, for example, housing 30, 702, 1002, 1402. Thus, retaining elements 50, 500, 600 act as single use containers where there is no possibility to detach retaining elements 50, 500, 600 from housing and refill with more of shaving aid 102, 103, 708, 1008, 1308, 1408, 1608.

However, it is contemplated by the present disclosure to have retaining elements 50, 500, 600 that are selectively removable and reconnectable to housing, for example, housing 30, 702, 1002, 1402, to refill with more of shaving aid 102, 103, 708, 1008, 1308, 1408, 1608.

Thus, retaining elements 50, 500, 600 and housing, for example, housing 30, 702, 1002, 1402, can store shaving aid 708, 1008, 1308, 1408, 1608 and facilitate shaving without need for an inconvenient, large cartridge with additional components. Further, retaining elements 50, 500, 600 and the housing 30 can store shaving aid 102, 103, 708, 1008, 1308, 1408, 1608 to improve lubricity.

When a certain structural element is described as "is connected to", "is coupled to", or "is in contact with" a second structural element, it should be interpreted that the second structural element can "be connected to", "be coupled to", or "be in contact with" another structural element, as well as that the certain structural element is directly connected to or is in direct contact with yet another structural element.

It should be noted that the terms "first", "second", and the like can be used herein to modify various elements. These modifiers do not imply a spatial, sequential or hierarchical order to the modified elements unless specifically stated.

As used herein, the terms "a" and "an" mean "one or more" unless specifically indicated otherwise.

As used herein, the term "substantially" means the complete or nearly complete extent or degree of an action, characteristic, property, state, structure, item, or result. For example, an object that is "substantially" enclosed means that the object is either completely enclosed or nearly completely enclosed. The exact allowable degree of deviation from absolute completeness can in some cases depend on the specific context. However, generally, the nearness of completion will be to have the same overall result as if absolute and total completion were obtained.

As used herein, the term "about" is used to provide flexibility to a numerical range endpoint by providing that a given value can be "a little above" or "a little below" the endpoint. Further, where a numerical range is provided, the range is intended to include any and all numbers within the numerical range, including the end points of the range.

While the present disclosure has been described with reference to one or more exemplary aspects, it will be understood by those skilled in the art, that various changes can be made, and equivalents can be substituted for elements thereof without departing from the scope of the present disclosure. In addition, many modifications can be made to adapt a particular situation or material to the teachings of the present disclosure without departing from the scope thereof. Therefore, it is intended that the present disclosure will not be limited to the particular aspects disclosed herein, but that the disclosure will include all aspects that fall within the scope of the appended claims.

As is evident from the figures and text presented above, as well as the examples below, a variety of embodiments are contemplated:

1. A razor cartridge, the cartridge comprising: a housing having a portion that forms a cavity; a retaining element configured to maintain a blade in the housing, the retaining element having a top surface that includes an aperture therethrough, a bottom surface, and a side portion connecting the top surface to the bottom surface to define a volume between the top surface and the bottom surface, the retaining element connectable to the housing so that the cavity is fitted in the volume of the retaining element and a shaving aid is fitted in the cavity.

2. The cartridge of embodiment 1, wherein the shaving aid comprises a lubricating composition and a pusher material.

3. The cartridge of anyone of embodiments 1 or 2, wherein the aperture is a first aperture and the retaining element further comprises a second aperture therethrough also provided at the top surface, and wherein the first aperture and the second aperture are separated by a bar.

4. The cartridge of anyone of the preceding embodiments, wherein the housing has a hole in the cavity, the hole is provided in fluid communication with a further aperture provided on the bottom surface of the retainer.

5. The cartridge of anyone of the preceding embodiments, wherein the housing has a front edge, a rear edge, a pair of side edges connecting the front edge to the rear edge, the side edges having a top surface, a lateral surface and a bottom surface also connecting the front edge to the rear edge, wherein the lateral surface also connects the top and bottom surfaces of the housing, wherein the retaining element comprises a C-shape embracing at least in part the lateral surface of the side edge and extending over a portion of the top and bottom surfaces of the housing.

6. The cartridge of anyone of the preceding embodiments, wherein the C-shaped retaining element extends longitudinally along the side edge of the housing 7. The cartridge of anyone of the preceding embodiments, wherein the retaining element forms a snap-fit on at least a portion of a side edge of housing through a locking projection that is configured to anchor in a complementary groove of the housing, and wherein the retaining element has an interior bottom surface opposite the bottom surface that follows a shape of the portion of the housing side edge.

8. A razor cartridge, the cartridge comprising: a housing having a portion forming a cavity; a retaining element configured to maintain a blade in the housing, the retaining element having a top portion that includes an aperture therethrough, a bottom portion, and a side portion connecting the top portion to the bottom portion to define a volume between the top portion and the bottom portion, the retaining element connectable to the housing; and a shaving aid provided in the cavity of housing that is connected to the retaining element, the shaving aid having a lubricating composition and a pusher material.

9. The cartridge of embodiment 8, wherein the aperture is a first aperture and the retaining element further comprises a second aperture through the top surface, and wherein the first aperture and the second aperture are separated by a bar.

10. The cartridge of anyone of the embodiments 8 or 9, wherein the housing has a hole in the cavity, the hole is configured to match a further aperture provided on the bottom surface of the retainer 11. The cartridge of anyone of the embodiments 8-10, wherein the pusher material has a portion that is a superabsorbent material.

12. The cartridge of anyone of the embodiments 8-11, wherein the pusher material has a portion that absorbs water and/or humidity and swells thereby being able to push upwards the lubricating composition.

13. The cartridge of anyone of the embodiments 8-12, wherein the lubricating composition is a mixture of water-soluble and water-insoluble ingredients, such that the lubricating composition to maintain the same shape when coming in contact with water.

14. The cartridge of anyone of the embodiments 8-13, wherein the lubricating composition has a first portion separated from a second portion by the bar so that the first portion is dispensed through the first aperture and the second portion is dispensed through second aperture.

15. The cartridge of anyone of the embodiments 8-14, wherein the pusher material has a portion that forms a groove that is angled on opposite sides so that one of the sides directs the first portion of the lubricating composition outward away from the bar and the other side directs the second portion of the lubricating composition outward away from the bar.

16. The cartridge of anyone of the embodiments 8-15, wherein the housing has a front edge, a rear edge, a pair of side edges connecting the front edge to the rear edge, the side edges having a top surface, a lateral surface and a bottom surface also connecting the front edge to the rear edge, wherein the lateral surface also connects the top and bottom surfaces of the housing, wherein the retaining element comprises a C-shape embracing at least in part the lateral surface of the side edge of the cartridge and extends over a portion of the top and bottom surfaces of the housing.

17. A razor cartridge, the cartridge comprising: a housing having a portion forming a cavity; a retaining element configured to maintain a blade in the housing, the retaining element having a top portion that includes an aperture therethrough, a bottom portion, and a side portion connecting the top portion to the bottom portion to define a volume between the top portion and the bottom portion, the retaining element connectable to a side edge of the cartridge; and a shaving aid provided within the cavity of housing that is connected to the retaining element, the shaving aid being connected to the housing.

18. The cartridge of embodiment 17, wherein the shaving aid has a main body and a protrusion extending from the main body.

19. The cartridge of anyone of the embodiments 17 or 18, wherein the housing has a portion that mates with the protrusion of the shaving aid to connect/lock the shaving aid to the housing.

20. The cartridge of anyone of the embodiments 17-19, wherein the shaving aid is water activated in a rigid/solid state.

21. The cartridge of anyone of the embodiments 17-20, wherein the housing has a groove that mates with the protrusion of the shaving aid to connect/lock the shaving aid to the housing.

22. The cartridge of anyone of the embodiments 17-21, wherein the retaining element comprises a C-shape embracing at least in part the side edge of the cartridge and extends over a portion of a top and bottom surfaces of the housing.

What is claimed is:

1. A razor cartridge, the cartridge comprising:
a housing having a portion that forms a cavity, the housing having a front edge, a rear edge, a pair of side edges, a top surface, and a bottom surface, the front edge and the rear edge being longer than the pair of side edges, the pair of side edges each being on opposite sides of the housing;
a pair of retaining elements configured to maintain a blade in the housing, each of the pair of retaining elements having a top portion that includes at least one aperture therethrough, a bottom portion, and an intermediate portion connecting the top portion to the bottom portion to define an interior volume between the top portion and the bottom portion; and
a shaving aid fitted in the cavity,
each of the pair of retaining elements connectable to the housing so that the cavity is fitted within the interior volume of each of the pair of retaining elements, wherein each of the pair of retaining elements being connected to only one side edge of the pair of side edges.

2. The cartridge of claim 1, wherein the shaving aid includes a lubricating composition and a pusher material.

3. The cartridge of claim 2, wherein the at least one aperture is a first aperture and a second aperture provided through the top portion, the first aperture and the second aperture being separated by a bar.

4. A razor cartridge, the cartridge comprising:
a housing having a portion that forms a cavity;
at least one retaining element configured to maintain a blade in the housing, the at least one retaining element having a top portion that includes at least one aperture therethrough, a bottom portion, and an intermediate portion connecting the top portion to the bottom portion to define an interior volume between the top portion and the bottom portion; and
a shaving aid fitted in the cavity,
wherein the at least one retaining element connectable to the housing so that the cavity is fitted within the interior volume of the at least one retaining element, wherein the shaving aid includes a lubricating composition and a pusher material, and wherein the housing includes a hole and the bottom portion of the at least one retaining element includes a hole, the hole of the housing is in fluid communication with the hole in the bottom portion of the at least one retaining element.

5. The cartridge of claim 1, wherein,
each of the pair of retaining element embraces at least in part one of the pair of lateral surfaces and extends over a portion of the top surface and the bottom surface of the housing.

6. The cartridge of claim 5, wherein each of the pair of retaining elements is C-shaped and extends along a length of one of the pair of side edges of the housing.

7. The cartridge of claim 1, wherein each of the pair of retaining elements includes a locking projection that is configured to anchor in a complementary groove of the housing,
the locking projection and the complementary groove configured to allow the at least one retaining element to be snap-fit on at least a portion of one of the pair of side edges of housing such that an interior bottom surface of the retaining element conforms with a shape of the bottom surface of the housing.

8. A razor cartridge, the cartridge comprising:
a housing having a portion forming a cavity, the housing having a front edge, a rear edge, a pair of side edges, a top surface, and a bottom surface, the front edge and the rear edge being longer than the pair of side edges, the pair of side edges each being on opposite sides of the housing;
a shaving aid provided in the cavity of the housing, the shaving aid including a lubricating composition and a pusher material;
a retaining element configured to maintain a blade in the housing, the retaining element having a top portion that includes an aperture therethrough, a bottom portion, and an intermediate portion connecting the top portion to the bottom portion to define an interior volume between the top portion and the bottom portion, the retaining element being connectable to the housing and encompassing the shaving aid, wherein the retaining element being connected to only one side edge of the pair of side edges.

9. The cartridge of claim 8, wherein the aperture includes a first aperture and a second aperture formed through the top surface of the retaining element the first aperture and the second aperture being separated by a bar.

10. The cartridge of claim 9, wherein the housing includes a hole formed in the cavity, the hole is configured to match a hole provided in the bottom surface of the retaining element.

11. The cartridge of claim 8, wherein the pusher material includes a portion that absorbs water and/or humidity and swells thereby being capable of pushing the lubricating composition upwards.

12. The cartridge of claim 8, wherein the lubricating composition is a mixture of water-soluble and water-insoluble ingredients, such that the lubricating composition is capable of maintaining a shape when in contact with water.

13. The cartridge of claim 9, wherein the lubricating composition includes a first portion and a second portion, the first and second portions being separated by the bar so that the first portion is dispensed through the first aperture and the second portion is dispensed through second aperture.

14. The cartridge of claim 13, wherein the pusher material includes a portion that forms a groove that is angled on opposite sides so that one of the sides directs the first portion of the lubricating composition outward away from the bar and the other side directs the second portion of the lubricating composition outward away from the bar.

15. The cartridge of claim 8, wherein the retaining element embraces at least in part one of the pair of the lateral surfaces and extends over a portion of the top and bottom surfaces of the housing.

16. A razor comprising:
a cartridge connected to a handle;
the cartridge including a housing, a blade and a retaining element, the housing having a pair of side edges having a cavity, the cavity being provided with a shaving aid, the housing having a front edge, a rear edge, the pair of side edges, a top surface, and a bottom surface, the front edge and the rear edge being longer than the pair of side edges, the pair of side edges each being on opposite sides of the housing;
the retaining element including a top portion having an aperture formed therethrough, a bottom portion, and an intermediate portion connecting the top portion to the bottom portion to define an interior volume between the top portion and the bottom portion, the retaining element being configured to be connected to enclose the shaving aid and to maintain the blade in the housing, wherein the retaining element being connected to only one side edge of the pair of side edges.

17. The razor of claim 16, wherein the shaving aid includes a main body and a protrusion extending from the main body.

18. The razor of claim 17, wherein the housing includes a portion that mates with the protrusion of the shaving aid to connect the shaving aid to the housing.

19. The cartridge of claim 18, wherein the shaving aid is water activated in a solid state.

20. The cartridge of claim 2, wherein the pusher material forms a bottom layer relative to the lubricating composition which is a top layer, and wherein the pusher material absorbs water and humidity and swells to push upwards on the top layer of lubricating composition.

* * * * *